United States Patent [19]

Manner

[11] 4,031,126

[45] June 21, 1977

[54] DRYING OF DIALKYL PEROXYDICARBONATES

[75] Inventor: James A. Manner, Akron, Ohio

[73] Assignee: PPG Industries, Inc., Pittsburgh, Pa.

[22] Filed: Feb. 12, 1976

[21] Appl. No.: 657,526

[52] U.S. Cl. .......................... 260/463; 260/453 RZ
[51] Int. Cl.² ......................................... C07C 68/08
[58] Field of Search ............ 260/455 Z, 463, 610 A

[56] References Cited

UNITED STATES PATENTS

| | | | |
|---|---|---|---|
| 3,377,373 | 4/1968 | Lederer et al. | 260/463 |
| 3,634,331 | 1/1972 | Neddenriep | 252/455 Z |
| 3,773,690 | 11/1973 | Heinze et al. | 252/455 Z |
| 3,775,341 | 11/1973 | Barter | 260/463 |
| 3,917,544 | 11/1975 | Michel | 252/455 Z |
| 3,927,114 | 12/1975 | Suda et al. | 260/610 A |

OTHER PUBLICATIONS

J.A.C.S., vol. 78, No. 23, (1956), pp. 5963–5977.
Molecular Sieves; Linde Chem. (1959), p. 1.

*Primary Examiner*—Lewis Gotts
*Assistant Examiner*—D. R. Phillips
*Attorney, Agent, or Firm*—William M. Dooley

[57] ABSTRACT

Dialkyl peroxydicarbonates are prepared in aqueous reaction media, washed with water, and then dried with sodium sulfate, calcium chloride, or the like. Peroxydicarbonates, particularly heat-sensitive peroxydicarbonates, may be dried safely and more effectively with the use of molecular sieves by contacting substantially phase water free peroxydicarbonate with sieves. Contact between heat-sensitive peroxydicarbonate and sieves should be effected in a way that avoids abrupt, excessive warming of peroxydicarbonate.

8 Claims, No Drawings

DRYING OF DIALKYL PEROXYDICARBONATES

THE INVENTION

This invention relates to reducing the water content of dialkyl peroxydicarbonates such as di-n-propyl peroxydicarbonate and di-n-butyl peroxydicarbonate and liquid solutions of dialkyl peroxydicarbonates in inert, organic solvents.

Dialkyl peroxydicarbonates are widely used as initiators in the polymerization of unsaturated compounds such as ethylene, vinyl chloride, acrylamide, and styrene. The lower alkyl peroxydicarbonates in particular, such as diisopropyl peroxydicarbonate, are sensitive to shock and heat, and may decompose rapidly, even explosively at room temperatures. Diisoproyl peroxydicarbonate and di-n-butyl peroxydicarbonate are reportedly subject to explosive decomposition within 15 minutes at 30° C. For this reason, they are manufactured at low temperatures, e.g., 0° to 10° C. and are shipped and stored at even lower temperatures, e.g., −20° to −35° C.

Dialkyl peroxydicarbonates and solutions thereof in organic solvents may be made by reacting an alkyl chloroformate and an aqueous alkaline solution of hydrogen peroxide. See, for example, U.S. Pat. Nos. 3,108,093, 3,377,373, 3,657,311, 3,657,312, and 3,849,468. Water washing is then employed in order to remove soluble impurities such as sodium chloride. After the water wash, the organic peroxydicarbonate phase is separated from the aqueous phase but common phase separation techniques, such as decantation with visual observation of the interface, are imperfect. Consequently, some of the water phase is generally carried over into the organic percarbonate phase. In addition, water droplets suspended in the organic phase may be carried over regardless of the care taken in separating the phases. The water-wet organic phase is dried with a desiccant such as sodium sulfate, magnesium sulfate, calcium chloride, or mixtures of these, often at temperatures of 0° C. to 12° C. Substantially all residual phase water present may be removed, but some dissolved water remains. When the peroxydicarbonate is cooled further to a safe shipping and storage temperature, e.g., about −30° C., water separates in the form of sheets, clumps, or crystals of ice visible in liquid peroxydicarbonates and present, although not readily apparent, in solid peroxydicarbonates. This ice is undesirable where the percarbonates is to be used in water-free polymerization, and is often mistaken for harmful impurity or hazardous crystallized percarbonate. An improved drying method was needed in order to provide a more commercially acceptable product.

Liquid peroxydicarbonates containing ice may be dried simply by filtering out the ice. However, neat peroxydicarbonates or concentrated solutions of them, e.g., 60 weight percent or higher, become viscous at the low temperatures required for freezing out the water. Cooling a large amount may take considerable time, and filtration of viscous liquids is difficult. Moreover, solid peroxydicarbonates containing ice cannot be dried by filtration.

Molecular sieves have been used effectively for drying gases such as air, hydrogen, and ethylene, and organic liquids such as benzene, alcohols, hydrocarbons, fluorocarbons, esters, ethers, amines, amides, ketones, and others, such as acrylonitrile and pyridine.

However, in drying dialkyl peroxydicarbonates with molecular sieves instead of the conventional sodium sulfate, a significant problem is encountered. The presence of water droplets in a percarbonate dried with molecular sieves may lead to the formation of hot spots on contact with the sieves, which could initiate runaway decomposition of the percarbonate. In addition, if the percarbonate and the sieves are brought into contact improperly, the percarbonate may be warmed temporarily to a hazardous degree, again entailing risk of runaway decomposition.

It has now been determined that the dissolved water content of liquid dialkyl peroxydicarbonates and liquid solutions of dialkyl peroxydicarbonates may be reduced safely with the use of molecular sieves provided the material to be dried is substantially free of phase water, i.e., water present in the material as a separate phase such as droplets, when it is contacted with the sieves. Sieve drying is more effective than drying with magnesium or sodium sulfate or calcium chloride, and thus provides a more commercially acceptable product.

In one embodiment of this invention, the dissolved water content of dialkyl peroxydicarbonate is reduced by contacting substantially phase water free percarbonate with molecular sieves. In another embodiment, water-wet (i.e., phase water containing) dialkyl peroxydicarbonate is dried in two stages. First, substantially all phase water is removed and next, the dissolved water content is reduced with the use of molecular sieves.

It is important in the practice of this invention that the percarbonate, i.e., the dialkyl peroxydicarbonate, be substantially free of phase water when it is contacted with the sieves. The reason is that molecular sieves have a great affinity for water and a high heat of hydration. Considerable heat is released when water is adsorbed into molecular sieves, so much so that water will nearly boil when mixed with an equal weight of dry sieves. In the drying of thermally stable compounds this heat of hydration is no problem. However, in the drying of a heat-sensitive percarbonate, the release of a substantial quantity of heat could be dangerous.

For example, if a droplet of phase water in the percarbonate is adsorbed by a particle of molecular sieve, the heat of hydration thereby released could create a hot spot and initiate a rapid, self-propagating decomposition of all the percarbonate present. Diisopropyl peroxydicarbonate is said to decompose explosively at room temperature; thus any localized hot spots occurring in this percarbonate would be extremely hazardous. It should be noted that phase water contaminated di-n-propyl peroxydicarbonate and di-sec-butyl peroxydicarbonate have been dried with molecular sieves without mishap by both the column and tank agitation methods. However, the risk was appreciated, and no attempt would be made to dry such phase water contaminated materials routinely on a production scale without strong safety precautions such as shielding, bunkers, or possibly remote controls.

Any liquid dialkyl peroxydicarbonate may be dried effectively in accordance with this invention. The term "liquid dialkyl peroxydicarbonate" is intended to include both liquid dialkyl peroxydicarbonates and liquid solutions in inert, organic solvents of liquid and solid dialkyl peroxydicarbonates. "Liquid dialkyl peroxydicarbonates" are liquid at the drying temperature used, but may be liquid or solid if cooled to a storage temperature below the drying temperature. Dialkyl peroxydicarbonates wherein the alkyl groups are alkyl or cycloalkyl groups of 1 to 20 carbons or more may be dried in accordance with this invention.

They may be represented by the formula

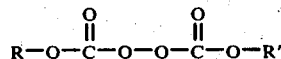

wherein R and R' independently are alkyl or cycloalkyl groups having 1 to 20 carbons, such as methyl, ethyl, n-propyl, t-butyl, cyclohexyl, 4-methycyclohexyl, 2-ethylhexyl, 3,3,5-trimethylcyclohexyl, and cetyl groups. R and R' are usually the same and are usually unsubstituted but they may be different, and may bear inert substituents, for example, halogen, notably chlorine, aryl groups such as phenyl and tolyl, alkyl groups such as methyl and t-butyl, and other substituents inert to peroxydicarbonates. Some of these dialkyl peroxydicarbonates are solids at room temperature and below, but may be dried in liquid solution form in accordance with this invention.

The practice of this invention is particularly beneficial for drying heat-sensitive dialkyl peroxydicarbonates, i.e., those which are customarily manufactured, shipped, or stored under refrigeration. The heat sensitivity of alkyl peroxydicarbonates depends upon the structure of the compound and primarily upon the ratio of carbon to active, peroxide oxygen. Solutions are more stable than neat liquids, and percarbonates of high molecular weight are more stable than those of lower molecular weight. In these percarbonates, R and R' are alkyl or cycloalkyl groups having from 1 to 8 carbons. Solutions of such percarbonates may also be heat-sensitive, depending on concentration.

Examples of heat-sensitive dialkyl peroxydicarbonates include dimethyl peroxydicarbonate, di(chloromethyl)peroxydicarbonate, diethyl peroxydicarbonate, diisopropyl peroxydicarbonate, di-n-butyl peroxydicarbonate, di-t-butyl peroxydicarbonate, dicyclohexyl peroxydicarbonate, dibenzyl peroxydicarbonate, and di-2-ethylhexyl peroxydicarbonate.

Other peroxydicarbonates which may be dried in accordance with this invention, usually in solution, for example, di(cis-3,3,5-trimethylcyclohexyl)peroxydicarbonate; didocecyl peroxydicarbonate, dicetyl peroxydicarbonate, di(4-t-butylcyclohexyl)peroxydicarbonate, dibornyl peroxydicarbonate, and di(3-tricyclo[4.4.0]decyl)peroxydicarbonate.

Solutions of dialkyl peroxydicarbonates in inert, organic solvents which are not appreciably adsorbed by the molecular sieves may be dried. Useful inert, organic solvents for dialkyl peroxydicarbonates include benzene, toluene, heptane, cyclohexane, dimethyl phthalate, methylcyclohexane, odorless mineral spirits, and other organic solvents inert to peroxydicarbonates.

Molecular sieves useful in the practice of this invention are crystalline metal alumino-silicate, zeolites, usually synthetic, that have been activated for adsorption by removal of water of hydration. They may be represented by the general formula $M_{2/n}O \cdot Al_2O_3 \cdot xSiO_2 \cdot yH_2O$, wherein M is a cation of $n$ valence, usually sodium or calcium. They are characterized by an open crystalline lattice having pores or apertures through which small molecules such as water can pass into the interior of the crystal, but through which larger molecules, such as dialkyl peroxydicarbonate, cannot pass.

Generally, any kind of molecular sieve may be used which is capable of adsorbing water from dialkyl peroxydicarbonate selectively, i.e., while adsorbing little or no percarbonate. Any of the known types of molecular sieve ordinarily used to dry organic liquids may be used in the practice of this invention. The general principles guiding the use of molecular sieves are well known, particularly the relation between the sieve pore size and the molecular size of the substance to be dried, and the amount of sieves required. Molecular sieves useful in the practice of this invention have a nominal free aperture diameter of between about 3 and 8 Angstroms, preferably 4 to 5 Angstroms. The maximum useful nominal free aperture diameter is determined by the molecular size of the percarbonate to be dried. Molecular sieves having 3 Angstrom apertures may dry more slowly than those with larger apertures.

Sieves are supplied commercially in the form of powder, pellets, granules, and beads, often compressed with a clay binder. Forms having good mechanical strength are preferred in order to avoid cloudiness in the dried product, particularly when the sieves are agitated with the percarbonate. U.S. Pat. No. 3,917,544 describes the preparation of alumina-bonded molecular sieve agglomerates having high mechanical strength. Clay-bonded beads have been used successfully, and may be more economical.

A particularly useful molecular sieve has the unit cell formula $Na_{12}[(AlO_2)_{12}(SiO_2)_{12}] \cdot 27H_2O$, a nominal free aperture of about 4 Angstroms, and is sold by Union Carbide Corporation under the designation LINDE Molecular Sieves Type 4A. Other zeolite alumino-silicate molecular sieves may also be used. Union Carbide Corporation's trade publication F-1979 B, entitled "LINDE Molecular Sieves," also describes molecular sieves useful in the practice of this invention.

The amount of sieves to be used may be determined in accordance with ordinary practice, depending upon the adsorbing capacity and physical form of the sieves, the water content of the percarbonate, contact time, degree of agitation, bed depth, flow rate, temperature, viscosity, and the extent of dryness desired. Generally, molecular sieves may be used in amounts effective to reduce the water content of the percarbonate, e.g., between about 0.1 and 10 weight percent, usually between about 1 and 5 weight percent, by weight of substantially phase water free percarbonate or solution thereof. The percarbonate and the molecular sieves are contacted for a time sufficient to reduce the water content of the percarbonate. Contact times may vary from about 1 minute to 1 hour or more. Preferably, the percarbonate and the sieves are contacted until the cloud point of the percarbonate is lowered substantially, desirably to below the anticipated shipping or storage temperature of the percarbonate. The adsorbing capacity of a particular type of sieve is lower when the sieves are used in a column than when they are used in a tank with agitation, owing to equilibrium and mass transfer phenomena in the column. Suppliers of molecular sieves supply information and advice on the use of their products. Aside from the considerations pointed out herein, i.e., the requirements of substantial absence of phase water and the need for care in contacting the sieves and the percarbonate, the manner of employing the sieves is in accord with common practice, and may be adapted to particular process conditions in the usual way.

Drying of dialkyl peroxydicarbonates with molecular sieves may be carried out at a variety of temperatures and pressures. The use of ambient atmospheric pressure is convenient, but higher or lower pressure may be used if desired, so long as the percarbonate or solution thereof remains in the liquid state. The choice of a suitable drying temperature for a particular percarbonate depends upon the stability of the percarbonate at higher temperatures and the viscosity at lower temperatures. Any temperature may be used at which the percarbonate or solution thereof is liquid, is stable enough for safe processing, and has low enough viscosity for convenient processing. The temperature customarily used for product work up of a given percarbonate may also be used for molecular sieve drying.

Principles governing the design and operation of systems employing adsorbents including molecular sieves are discussed in *Chemical Engineers' Handbook*, Robert H. Perry and Cecil H. Chilton, Editors, 5$^{th}$ Ed. (New York: McGraw-Hill, Inc.; 1973), section 16, "Adsorption and Ion Exchange."

For example, neat diisopropyl peroxydicarbonate may be dried safely at temperatures between about 10° and 16° C., preferably between about 11° and 13° C. Generally, for di- lower alkyl peroxydicarbonates having 1 to 8 carbons in each alkyl group, temperatures within the range between about 5° and 20° C. will be useful. For percarbonates having higher alkyl groups, correspondingly higher temperatures may be used. Solutions of percarbonates tend to be less viscous and more stable than neat percarbonates, and may therefore be dried over an even wider range of temperature.

Some care may be required in bringing the sieves and the percarbonate into contact, particularly when a relatively small amount of percarbonate contacts a large quantity of sieves. This may occur, for example, when percarbonate is first passed into a column of sieves, or when percarbonate is first poured onto a mass of sieves at the bottom of a drying vessel.

When certain phase water free peroxydicarbonates were introduced into columns packed with room-temperature (20°-22° C.) molecular sieves, significant warming was noted in the first portion of percarbonate flowing from the column. Although the percarbonate was poured into the column at 7°-10° C., the first portion of effluent was as warm as 21° C. After a minute or 2, the temperature of the effluent fell as the column cooled. Of course, heat transfer from the sieves and heat of hydration caused most of the warming, but in addition there appeared to be a small interaction between percarbonate and sieves, even when the percarbonate had already been dried with sieves, which contributed heat. In any event, the warming, though transitory, is hazardous when a heat-sensitive percarbonate such as diisopropyl peroxydicarbonate is being dried. If a column of sieves is to be used for drying heat-sensitive percarbonate, pre-cooling of the sieves is advised.

During the drying of a heat-sensitive dialkyl peroxydicarbonate, it is advisable at all times to avoid any abrupt, substantial rise in temperature and to maintain the temperature of the percarbonate within a safe range. Because this specification is directed to those already familiar with the manufacture or handling of dialkyl peroxydicarbonates, it is not necessary to set forth in detail the precise temperature limits for each percarbonate. The known limits apply also to the practice of this invention. It is herein pointed out that careless use of molecular sieves in the drying of a dialkyl peroxydicarbonate may inadvertently cause excessive warming of the percarbonate.

To reduce the risk of excessive warming, care should be taken to provide adequate cooling, particularly when the percarbonate and the sieves are first brought into contact. Because a relatively small weight percent of sieves is normally used, the sieves may be added to the percarbonate in a tank with agitation, so that any heat generated will be dispersed quickly through the bulk of percarbonate. Sieves in a column may be pre-cooled. The tank agitation method avoids the need for cooling the sieves before use. Any method of bringing the sieves and the percarbonate into contact which allows for a rise of no more than about 5° C. in the temperature of the percarbonate at any time is satisfactory for use even with the most heat-sensitive dialkyl peroxydicarbonates, such as diisopropyl peroxydicarbonate.

After the percarbonate has been dried, the used sieves may be discarded or they may be washed free of percarbonate with a suitable solvent, dried, and regenerated by heating in the usual way. Considering the relatively small quantity of sieves used and the hazardous nature of many percarbonates, disposal is preferable.

In order to dry water-wet dialkyl peroxydicarbonate safely with the use of molecular sieves, it is necessary first to remove substantially all phase water present in the percarbonate. Although gross phase separation techniques remove a significant proportion of phase water, further treatment will generally be required to remove substantially all residual traces of phase water present. The presence of phase water may be discovered by visual observation of a sample or by near infrared spectroscopy.

A convenient measure of the water content of a liquid dialkyl peroxydicarbonate is the cloud point. In the tests reported in this specification, cloud points were determined by placing about 80 milliliters of the peroxydicarbonate liquid or solution in a 4 ounce glass bottle containing a magnetic stirring bar. A thermometer in a rubber stopper was inserted to about 1 inch from the bottom. The bottle was then partially immersed (about two-thirds in a dry ice-acetone bath and stirring was started. The sample was cooled until it became cloudy with ice crystals or too viscous to stir. The temperature at which cloudiness was first observed was reported as the cloud point.

A dialkyl peroxydicarbonate or solution thereof may be considered substantially phase water free when it has a cloud point, as determined by the method described above, of below −1° C., preferably below about −5° C., or when its total water content is no more than the solubility of water therein at the desired drying temperature. For example, the solubility of water in di-n-propyl peroxydicarbonate (NPP) at 10° C. is 0.25 percent by weight. Thus, a sample of NPP to be dried at 10° C. may be considered substantially phase water free if its total water content is 0.25 weight percent or less. Any method for removal of phase water which produces a product having a cloud point or total water content at or below the indicated values is satisfactory.

Percarbonate which contains phase water may be contacted with a conventional desiccant such as sodium sulfate, magnesium sulfate, calcium chloride, mixtures of these, or another desiccant of comparable drying power, until substantially all phase water is removed. The use of such desiccants, which have a lesser affinity for water and lower heat of hydration then molecular sieves, does not entail a significant risk of run-away decomposition, especially when used in the customary tank agitation manner.

The use of a liquid-liquid centrifuge for removing substantially all phase water is preferred. A liquid-liquid centrifuge may be operated continuously and reduces the need for handling and disposal of desiccants contaminated with hazardous percarbonate. This type of centrifuge is well known. See, for example, McCabe and Smith, *Unit Operations of Chemical Engineering*, 2$^{nd}$ Ed. (New York: McGraw-Hill Book Company, 1967), pp. 923-925. The centrifuge separates immiscible liquids by specific gravity; a useful one may be chosen on the basis of desired feed rate and the specific gravities of the liquids to be separated. Dialkyl peroxydicarbonates and solutions thereof may have specific gravities higher or lower than that of water. A liquid-liquid centrifuge may be used effectively in accordance with this invention when the specific gravities of the liquids to be separated differ by about 0.1 units. Generally, if two immiscible liquids will separate upon standing, they may be separated effectively with a liquid-liquid centrifuge. The high shear action of such a centrifuge tends to break emulsions and provide very efficient phase separation. A unit which produces substantially phase water free dialkyl peroxydicarbonate when operating at the desired safe processing temperature is required. With the desired performance criteria in mind, a suitable unit may be selected without difficulty. Suitable units are reportedly available commercially. A preferred material of construction for all wetted parts is stainless steel, and stainless steel units are also reportedly available on the market.

The following examples illustrate ways in which the present invention may be practiced.

EXAMPLE I

A liquid-liquid centrifuge capable of separating liquids whose specific gravities differ by 0.1 units and having a through-put capacity of up to 0.75 gallons per minute was employed. The unit was a DeLaval Gyro Tester Centrifuge obtained from the DeLaval Separator Co. Other comparable units are reportedly available.

Two 1 gallon samples of di-sec-butyl peroxydicarbonate (SBP) were each mixed with about 1 pint of water. The centrifuge was fed first with dried SBP and then water until material was coming from both the heavy and light phase discharge outlets of the centrifuge. One gallon of the wet SBP feed was then introduced at a rate of about 140 to 150 cubic centimeters per minute, and samples 1 and 2 were taken after 15 and 25 minutes. The second gallon of wet SBP was fed at 175 to 180 cubic centimeters per minutes, and samples 3 and 4 were taken after 15 and 25 minutes. Feed temperature was about 5° C. (40° F.); discharge temperature was about 6° C. (41°-43° F.).

A sample of SBP from which phase water had been decanted was dried by contact with 3 percent by weight of SBP of anhydrous $Na_2SO_4$ for a period of 10 to 20 minutes with agitation.

The following cloud points were found:

| | |
|---|---|
| Wet SBP Feed | >10° C. (50° F.) |
| Samples 1 and 2 | −4° C. (25° F.) |
| Samples 3 and 4 | −2° C. (28° F.) |
| $Na_2SO_4$ Dried SBP | −10° C. (14° F.) |

Thus, both centrifuge drying and $Na_2SO_4$ drying give substantially phase water free product.

To a sample of centrifuge dried SBP, 3 weight percent anhydrous $Na_2SO_4$ was added. To another sample, 3 weight percent LINDE Type 4A molecular sieves, 8–12 mesh beads, was added. Both samples were agitated, and the following cloud points found:

| | |
|---|---|
| Centrifuge Product + 3% $Na_2SO_4$ | |
| after 10 minutes agitation | −5° C. (23° F.) |
| after 20 minutes agitation | −7° C. (19° F.) |
| Centrifuge Product + 3% Molecular Sieves | |
| after 10 minutes agitation | −27° C. (−16° F.) |
| after 20 minutes agitation | <−40° C. (−40° F.) |

As noted earlier, heat sensitive dialkyl peroxydicarbonates such as SBP are usually shipped and stored at temperatures in the range of about −20° to −35° C. The results above show that molecular sieves are much more effective than sodium sulfate in drying substantially phase water free SBP. After only 10 minutes agitation, molecular sieves lowered the cloud point of SBP to below part of the storage temperature range. After 20 minutes, the cloud point was below the lowest commonly used storage temperature. Thus SBP dried in accordance with this invention does not display objectionable ice separation under typical storage conditions and therefore is a more commercially acceptable product than SBP dried with $Na_2SO_4$ under similar conditions. The lowest cloud point attainable with $Na_2SO_4$ on a practical production basis would be about −10° C.

EXAMPLE II

About 200 pounds (91 kilograms) of di-n-propyl peroxydicarbonate (NPP) was dried by agitation with 3 weight percent anhydrous sodium sulfate until it had a cloud point of −13° C. (8° F.). Seven pounds, 2 ounces (3.24 kilograms, 3.5 percent by weight of NPP) of LINDE Type 4A molecular sieves, 8–12 mesh beads, was placed in a polyethylene column, forming a bed 4.5 inches (11.4 centimeters) wide and about 16.5 inches (41.9 centimeters) high. Thermometers were placed in the column at the top and bottom. The NPP was poured onto the top of the sieve bed and collected at the bottom in about 10.5 pound (4.8 kilogram) portions. A total of 18 portions were collected. The table below shows the temperatures of the NPP at the top and bottom of the column and cloud points measured for selected samples. Flow rate was 10.5 pounds per 2 minutes.

| Sample No. | Temperature, ° C. Top | Bottom | Cloud Point, ° C. |
|---|---|---|---|
| 1 | 10 | 21 | <−43 |
| 10 | 10 | 12 | −42 |
| 15 | 9.5 | 11.5 | −34 |
| 18 | 9.5 | 11.5 | −33 |

The bottom temperature for Sample 1 was a transient localized in the first portion of material through the column. This undesirably high, potentially hazardous temperature peak can be substantially avoided by cooling the sieves, preferably to the temperature of the percarbonate or lower, before introducing the percarbonate.

The foregoing examples illustrate drying of dialkyl peroxydicarbonate which may be practiced on a practical scale in accordance with this invention. Of course, not all modes of practicing the invention will be equally efficient or desirable. The use of granular sieves may lead to haziness in the dried product, owing to dust from the granules. The use of larger particles than the 8–12 mesh beads used in the examples may require slower flow rates or longer contact time to achieve comparable dryness. Molecular sieves having 3 Angstroms openings rather than the 4 Angstroms of LINDE Type 4A may adsorb more slowly and require slower flow rates. Percarbonate having a relatively high cloud point, e.g., 0° C., may require the use of a greater quantity of molecular sieves than the 3 to 3.5 weight percent used in the examples. However, these matters are routinely considered in developing a working drying procedure using molecular sieves, and are thus not peculiar to the practice of this invention.

Although this invention has been described in terms of particular details and embodiments, the particulars of the description are not intended to limit the invention, the scope of which is defined in the following claims.

I claim:

1. A process for reducing the dissolved water content of dialkyl peroxydicarbonate, which comprises:
   contacting liquid dialkyl peroxydicarbonate with molecular sieves which selectively adsorb water from the peroxydicarbonate, the peroxydicarbonate containing dissolved water but being substantially free of phase water.

2. The process of claim 1, wherein the dialkyl peroxydicarbonate is heat-sensitive and has a cloud point below about −5° C., and which further comprises maintaining the temperature of the dialkyl peroxydicarbonate within a safe range at all times during the drying.

3. The process of claim 2, wherein the alkyl groups of the heat-sensitive dialkyl peroxydicarbonate independently are alkyl or cycloalkyl groups having 1 to 8 carbons.

4. A process for reducing the water content of dialkyl peroxydicarbonate, which comprises:
   a. removing substantially all phase water from the dialkyl peroxydicarbonate, and
   b. contacting liquid, substantially phase water free peroxydicarbonate from step (a) with molecular sieves which selectively adsorb dissolved water from the dialkyl peroxydicarbonate.

5. The process of claim 4, wherein substantially all phase water is removed from liquid dialkyl peroxydicarbonate with the use of a liquid-liquid centrifuge.

6. The process of claim 4, wherein substantially all phase water is removed from liquid peroxydicarbonate with the use of a desiccant selected from the group consisting of sodium sulfate, magnesium sulfate, calcium chloride, and mixtures thereof.

7. The process of claim 4, wherein the dialkyl peroxydicarbonate is heat-sensitive, and wherein the substantially phase water free peroxydicarbonate has a cloud point below about −5° C.

8. The process of claim 7, wherein the alkyl groups of the heat-sensitive dialkyl peroxydicarbonate independently are alkyl or cycloalkyl groups having 1 to 8 carbons.

* * * * *